(12) United States Patent
Häcker

(10) Patent No.: US 12,357,806 B2
(45) Date of Patent: Jul. 15, 2025

(54) METHOD FOR DISCONNECTION

(71) Applicant: FRESENIUS MEDICAL CARE DEUTSCHLAND GMBH, Bad Homburg (DE)

(72) Inventor: Jürgen Häcker, Neu-Anspach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 483 days.

(21) Appl. No.: 18/007,564

(22) PCT Filed: Jun. 2, 2021

(86) PCT No.: PCT/EP2021/064726
§ 371 (c)(1),
(2) Date: Dec. 1, 2022

(87) PCT Pub. No.: WO2021/245110
PCT Pub. Date: Dec. 9, 2021

(65) Prior Publication Data
US 2023/0218879 A1  Jul. 13, 2023

(30) Foreign Application Priority Data
Jun. 5, 2020 (DE) ............ 10 2020 114 988.3

(51) Int. Cl.
*A61M 39/10* (2006.01)
*A61M 1/36* (2006.01)
(Continued)

(52) U.S. Cl.
CPC ........ *A61M 39/10* (2013.01); *A61M 1/36222* (2022.05); *A61M 1/3644* (2014.02);
(Continued)

(58) Field of Classification Search
CPC .............. A61M 39/10; A61M 1/36222; A61M 1/3644; A61M 60/113; A61M 60/279;
(Continued)

(56) References Cited

U.S. PATENT DOCUMENTS 4,269,708 A * 5/1981 Bonomini ........... A61M 1/1696
210/90
5,336,051 A * 8/1994 Tamari ................ A61M 1/3621
417/474
(Continued)

FOREIGN PATENT DOCUMENTS

DE  102007024463 A1  11/2008
DE  102009024575 A1  10/2009
(Continued)

OTHER PUBLICATIONS

Office Action issued in corresponding Japanese Patent Application No. 2022-574518 dated Mar. 13, 2025 (5 pages).

*Primary Examiner* — Ariana Zimbouski
*Assistant Examiner* — Alessandro R Del Priore
(74) *Attorney, Agent, or Firm* — Kilyk & Bowersox, P.L.L.C.

(57) ABSTRACT

The present invention relates to a method for disconnecting two fluid-conducting line sections of a medical device which are detachably interconnected, wherein a first line section of the two line sections has at least partially an elastic property. The method comprises the steps of enclosing a fluid volume in the two line sections, generating a reduced pressure in the two line sections, as a result of which elastic deformation from a starting position into a tensioned position takes place in and/or on the first line section, wherein a fluid volume contained in the first line section is lower in the tensioned position than a fluid volume contained in the starting position, and detaching the connection of the line sections, wherein the fluid volume contained in the first line section
(Continued)

in the tensioned position increases. Furthermore, the invention relates to a medical device which is configured to carry out a method of this kind.

16 Claims, 12 Drawing Sheets

(51) Int. Cl.

| | |
|---|---|
| *A61M 60/113* | (2021.01) |
| *A61M 60/279* | (2021.01) |
| *A61M 60/37* | (2021.01) |
| *A61M 60/424* | (2021.01) |
| *A61M 60/585* | (2021.01) |

(52) U.S. Cl.
CPC ........ *A61M 60/113* (2021.01); *A61M 60/279* (2021.01); *A61M 60/37* (2021.01); *A61M 60/424* (2021.01); *A61M 60/585* (2021.01); A61M 1/3622 (2022.05); A61M 2039/1016 (2013.01)

(58) Field of Classification Search
CPC .. A61M 60/37; A61M 60/424; A61M 60/585; A61M 1/3622; A61M 2039/1016; A61M 2205/3351; A61M 1/3643; A61M 1/36226; A61M 2205/0216; A61M 2205/273; A61M 1/168; A61M 1/3653; A61M 2039/1027; A61M 39/1011; A61M 1/3646; A61M 1/3647; A61M 1/3649; A61M 1/365; A61M 1/3652; Y10S 604/905
See application file for complete search history.

(56) References Cited

U.S. PATENT DOCUMENTS

| | | | |
|---|---|---|---|
| 6,758,971 B1* | 7/2004 | Haight | A61M 1/3644 |
| | | | 210/136 |
| 8,398,577 B2 | 3/2013 | Burnett | |
| 2005/0063860 A1* | 3/2005 | Carpenter | A61M 60/113 |
| | | | 604/4.01 |
| 2009/0318844 A1 | 12/2009 | Burnett | |
| 2016/0243347 A1 | 8/2016 | Geiger et al. | |
| 2023/0000510 A1* | 1/2023 | Brady | A61M 1/743 |

FOREIGN PATENT DOCUMENTS

| | | |
|---|---|---|
| DE | 102013011717 A1 | 1/2015 |
| JP | 2010527247 A | 8/2010 |
| JP | 5356853 | 12/2013 |

\* cited by examiner

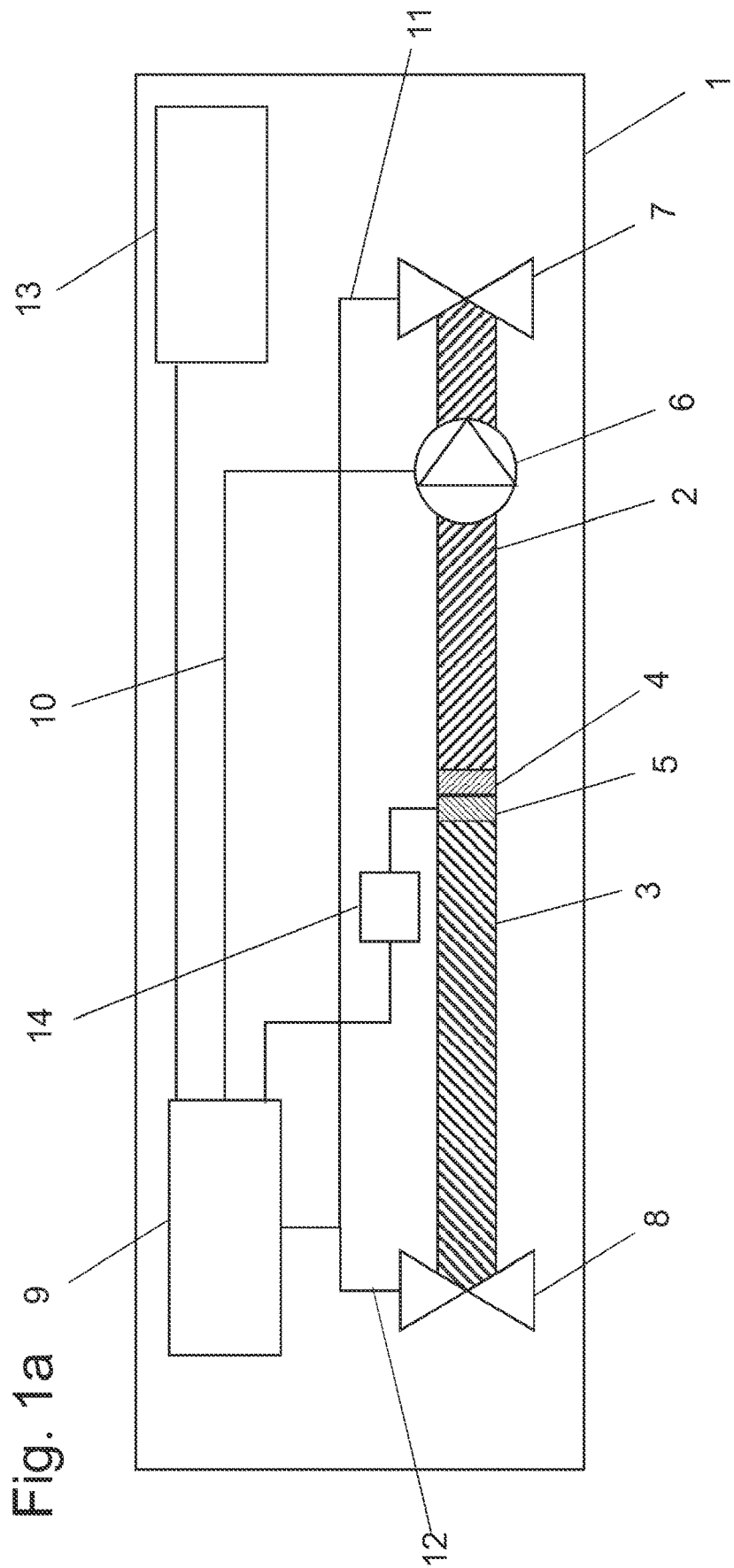

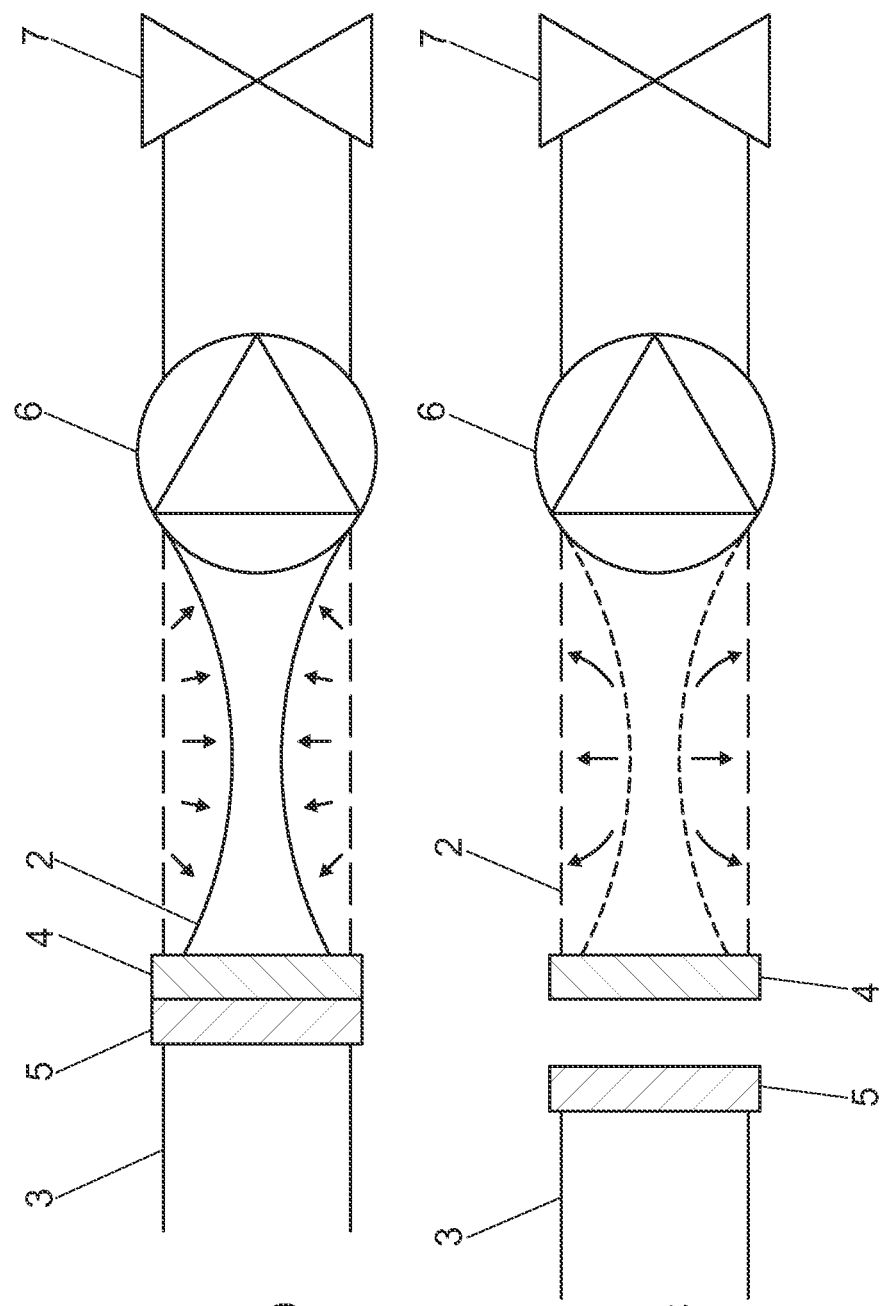

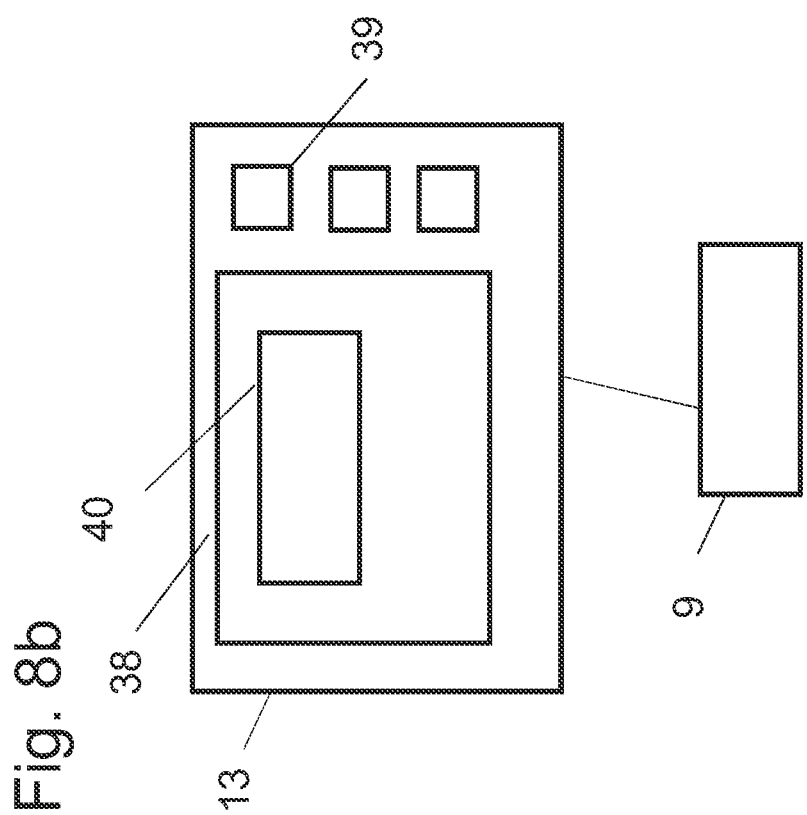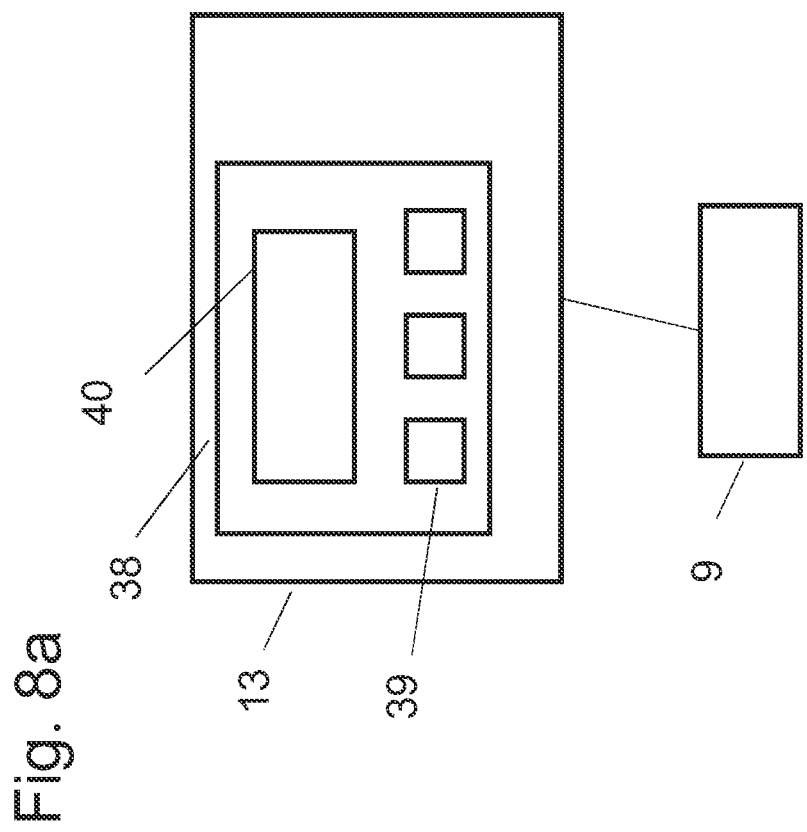

METHOD FOR DISCONNECTION

The present invention relates to a method for disconnecting fluid-conducting line sections of a medical device and to a medical device which is designed to perform a method according to the invention.

When disconnecting fluid-conducting line sections of a medical device from one another, such as a machine-side fluidic system from a fluidic system intended for single use (disposable) of extracorporeal blood-treatment machines or dialysis machines, high hygiene standards need to be maintained in order to ensure patient safety.

In practice, after extracorporeal blood treatment, when decoupling a tube set from a blood-treatment machine, liquid contained in the tube set can get into the device-side fluid circuit or the hydraulics of the device and contaminate it, which makes it necessary to perform time-consuming disinfection processes on the blood-treatment machine.

Before the start of treatment, there may be air, for example in the form of air bubbles, or contaminants in the liquid in the fluidic system of a medical device following a priming process (process of filling and flushing a fluid-line system with physiological liquid). If the fluidic system is disconnected in order to connect part of the fluidic system to a patient, as little air as possible should remain in the part of the fluidic system to be connected to the patient. If air or contaminants remain in the part of the fluidic system to be connected to the patient, this/these can get into the patient's bloodstream.

Furthermore, in particular in the medical field, it is desirable for leaks to be prevented when any fluid-conducting lines are disconnected for reasons of hygiene.

The problem addressed by the present invention is therefore that of mitigating or even entirely overcoming the problems from the prior art. In particular, the problem addressed by the present invention is that of providing a method for more hygienically disconnecting fluid connections and a corresponding medical device.

This problem is solved by the subject matter of the independent claims. The dependent claims relate to advantageous developments of the invention.

A method according to the invention for disconnecting two fluid-conducting line sections, in particular of a medical device, which are detachably interconnected, wherein a first line section of the two line sections has at least partially an elastic property, comprises the following steps:

enclosing a fluid volume in the two line sections,
  generating a reduced pressure in the two line sections, as a result of which elastic deformation from a starting position into a tensioned position takes place in and/or on the first line section, wherein a volume contained in the first line section is lower in the tensioned position than a volume contained in the starting position,
  detaching the connection of the line sections, wherein the fluid volume contained in the first line section in the tensioned position increases and the first line section moves back from the tensioned position towards the starting position.

The term "fluid" covers liquids, gases, and mixtures of liquids and gases in dissolved form (no interface) or undissolved form (with interface). The teaching set out here can, for example, be used when disconnecting two line sections which are completely filled with liquid or completely filled with gas or with liquid and gas, in particular also with a liquid-filled system that is connected to a gas reservoir or with a gas-filled system that is damp, for example still contains droplets.

The method may comprise a step in which the line sections are filled with liquid.

The term "fluid volume" means an enclosed quantity. By applying the reduced pressure, part of the enclosed quantity is removed from the enclosed volume (in the sense of a geometric volume), i.e. the fluid volume is decreased. The response may involve the geometric volume being reduced by a tube diameter being reduced, for example. This is primarily the case for liquids that virtually cannot be compressed or expanded. If the enclosed volume is partially filled with gas, this gas can expand, particularly in the case of a fixed-volume geometric volume if some of the liquid/gaseous material is removed from the enclosed volume. Combinations of a reduction in the geometric volume and an expansion of a gas with a decrease in the fluid volume are also possible.

"Elastic" or "more elastic" means that the line section in question undergoes an increase in the fluid volume contained therein when disconnecting the connection without external forces being involved. For example, the line section can exhibit contraction in response to the reduced pressure (smaller geometric volume in the following) and, during the disconnection, can exhibit relaxation together with an increase in volume due to the restoring force intrinsically inherent to the line section, and can cause fluid to flow in. In this process, the line section can, but does not have to, return to the starting volume again. For a gas, "elastic" can mean that gas or liquid flows in when the reduced pressure is removed, such that the pressure in the gas phase is equalized with the ambient pressure (approximately in accordance with the ideal gas law). The gas having lower pressure is likewise covered by the term "tensioned position" and the expansion or compression is covered by the term "deformation". "More elastic" means that the increase in volume in the line section in question is greater than in a comparative line section.

In other words, the relaxation of a deformed elastic line section or reduced pressure prevailing in a line section can be used to conduct fluid, in particular gas or liquid, away from a connection region of two line sections in a targeted manner when detaching a connection.

For example, by generating the reduced pressure, deformation of the first line section is generated in which the inner walls of the line curve inwards into the lumen, and therefore the flow cross section is narrowed. By means of the restoring force of the elastically deformed line section, the inner walls of the line move back towards the starting position and the volume contained by the first line section, for example the flow cross section, is enlarged again, meaning that fluid is drawn into the previously narrowed region.

By setting or selecting the material and/or the geometry, for example the length, tube diameter, wall thickness, tube-diameter geometry, deflection, in or of at least one region of the first line section and/or the second line section and/or by providing gas, for example in the form of a gas reservoir, in the first and/or second line section, the elastic property of the first line section and/or the second line section of the two line sections can be predetermined and therefore fluid can be guided out of the connection region towards one or both line sections in a targeted manner when the line sections are disconnected from one another, in particular towards the first line section when it has the elastic property. The restoring force can, for example, also develop by a tube which is compressed returning to its round shape again or by a more bent tubular line section being bent further by applying the reduced pressure and then straightening out again or by a stretched tube returning to its shortened length again.

The first line section and the second line section have an inner volume for receiving the fluid. Neither of the two line sections is a cover or cap. As intended, the first line section and the second line section are provided for liquid to be conveyed therethrough during use.

The first line section may be elastic at least in one region, such that at least this region undergoes contraction when reduced pressure is applied. When opening the connection to the second line section, liquid can be moved from the disconnection point towards the relaxing section of the first line section when the volume of the tube increases, due to the elasticity and the associated restoring force of the line section.

In the context of the present invention, a region of the first and/or second line section or the entire first and/or second line region may have an elastic property.

The fluid can be moved in the first line section (relatively elastic material or geometry in the first line section and relatively rigid material or geometry in the second line section) or in the second line section (relatively elastic material or geometry in the second line section and relatively rigid material or geometry in the first line section) in an increased manner.

The first line section may comprise at least one region which is more elastic than the second line section. As a result, the reduction in volume when the reduced pressure is applied is greater in the first line section than in the second line section. During the disconnection, the first line section undergoes a greater increase in volume and more liquid can be moved towards the first line section than towards the second line section.

The first line section and the second line section may each comprise at least one region which is made of a more elastic material than the remainder of the first line section and the second line section, wherein the region of the first line section is made of a more elastic material than the region of the second line section, such that, when the connection between the line sections is detached, fluid is drawn from a connection region of the line sections into the first line section to a greater extent than into the second line section.

In other words, the first line section and, optionally, the second line section may comprise a region which is more elastic than the second line section or the remainder of the first line section and the second line section, respectively. However, the entire first line section may also be more elastic than the entire second line section.

It is clear from that described above that a longer tube section can have greater elasticity than a shorter tube section (with the geometry and material otherwise being the same).

The first line section may be longer than the second line section.

The first line section and/or the second line section may be partially filled with a gas, for example air, while the remainder of the first and second line section may be filled with a liquid. The gas-filled region cannot be directly connected to a connection region between the first line section and/or the second line section and/or cannot be transferred out of the first line section and the second line section while the reduced pressure is being generated.

For example, a pump can pump liquid out of the first line section and/or the second line section. This decrease in fluid volume results in a larger volume being available for the gas that is provided in a gas reservoir and is fluidically connected to the first and/or second line section, and therefore said gas expands and the pressure in the gas drops.

If the connection between the first line section and the second line section is then disconnected, the gas contracts again (pressure equalization) and liquid can simultaneously be drawn out of the other line section and/or gas can be drawn from the surroundings via the disconnection point towards the gas.

The method for disconnection may comprise the step of closing a shut-off element arranged along the second line section, at one end of which another shut-off element is already arranged. As a result, the length of the second line section can be reduced. In particular, it may therefore be possible for the fluid to preferably be drawn into the first line section (for example into a tube set or another disposable item or, for example, into the internal fluidic system of a medical device) due to the differing elastic property. A medical device according to the invention may be equipped with a valve of this kind.

Movement of liquid of this kind that is directed in a targeted manner can be used to reduce the risk of undesired material in the liquid getting into the second line section from the first line section or getting into the second line section from the surroundings. As a result, it may be possible for a contamination risk of a reusable fluidic system to be reduced or for the quantity of air that gets into a tube set to be connected to a patient to be reduced.

The region having the elastic property may for example be a line loop or a pump line section of a pump, in particular a peristaltic pump. During the pump process, the line loop or the pump line section of a peristaltic pump is compressed by one or more actuators, for example rollers or fingers, and relaxed when the effect of the actuator(s) is removed. Primarily in pumps comprising rollers as actuators, the line loop can also be subjected to tensile forces, which can result in a reduction in the volume. The line loop or the pump line section of a pump of this kind, or on which the actuators of a pump of this kind act, routinely comprises a softer material or more elastic material than other line sections of the first and/or second line section. By the line loop or pump line section being used as a region having greater elasticity, a more elastic line section provided specifically for the purpose of the disconnection method disclosed here can be dispensed with. As a result, it may be possible to provide a more cost-effective, material-saving solution. In addition, the actuator of the peristaltic pump may also be used as a shut-off element. As a result, it may be possible to make further savings on costs and material, since a separate component for enclosing the fluid volume is not required.

Alternatively or additionally, both the first line section and the second line section may also comprise a region having an elastic property. The remainder of the line region in question may be made of a relatively rigid material here.

In this embodiment, the relaxation of the regions made of elastic material assists the separation of the fluid column when disconnecting the line sections. Fluid is moved from the connection region into both the first and second line section, meaning that leaks are prevented and hygiene is improved.

In this case, too, the elastic region of one line section may be more elastic than the elastic region of the other line section, such that the fluid is preferably moved towards the more elastic region.

The method according to the invention can be performed when a patient is not yet connected to a device performing the method.

A method according to the invention can therefore be used for preparing a medical device before the treatment, for example during the priming of the tube set used or when connecting or coupling the required lines, and for post-processing of a medical device after the treatment, for example when disconnecting or decoupling the required lines or disposing of used disposable items.

The method according to the invention therefore does not act upon the patient's body, but rather is carried out on the device side and on the disposable items connected thereto, or on other components that are fluidically coupled to the device.

Another aspect of the present invention relates to a medical device.

The medical device may be designed to carry out a method for disconnection or may be designed such that a method for disconnection can be carried out on this medical device, the method for disconnection including disconnecting at least two fluid-conducting line sections, which are detachably interconnected. A first line section of the two line sections has at least partially an elastic property.

The medical device may comprise at least one first and one second shut-off element for enclosing a fluid volume in the two line sections, a pump for generating a reduced pressure in the two line sections, as a result of which elastic deformation of the first line section from a starting position into a tensioned position can take place, and a controller for actuating the pump, wherein the controller is programmed to operate the pump to generate the reduced pressure in a disconnection mode.

The medical device may comprise means for enclosing a fluid volume in the two line sections and means for generating a reduced pressure in the two line sections, as a result of which elastic deformation of at least a region of the first line section from a starting position into a tensioned position takes place, such that, when detaching the connection of the two line sections, at least the region of the first line section returns to the starting position from the tensioned position, as a result of which fluid is drawn from a connection region of the line sections into the first line section.

The controller may be programmed to close one of the shut-off elements before the reduced pressure is generated. This means that the fluid volume can be closed on one side. Alternatively or additionally, the controller may be programmed to close one of the shut-off elements after the reduced pressure is generated. This means that the fluid volume can be enclosed.

The controller may actuate at least one, some or all the active components from the group of the means for generating the reduced pressure and the enclosing means. For example, the controller may be programmed to start a pump and to therefore generate a reduced pressure and/or to close a valve or clamp and to therefore produce a closed system.

The first or the second line section may be part of a device-side fluidic system of the medical device.

The medical device may further comprise a fluid source, in particular a physiological liquid source, which is fluidically connected to the second line section, optionally, a sterile filter fluidically arranged between and fluidically connected to the fluid source and the second line section, and a medical-device-side connector on one end of the second line section for connection to one end of the first line section.

In this embodiment, the medical device may be configured to supply the physiological liquid to the first line section via the second line section, for example by means of a pump, in a priming process and/or during the treatment through the sterile filter, which can retain contaminants, wherein the first line section may form part of a tube system and may be connected to a tube system which is filled with blood during the treatment. After the treatment, the first line section can be detached from the second line system and disposed of, for example, using the method according to the invention or in the disconnection mode. The second line section can remain in the medical device and can be reused in a subsequent treatment.

The medical device may comprise a discharge line, wherein the first line section can be fluidically connected to the discharge line or can form a part thereof. The medical device may further comprise a medical-device-side connector on one end of the first line section for connection to one end of the second line section.

In this embodiment, the second line section may be part of a line that conducts blood during blood treatment. During a priming process, the second line section can be detachably connected to the first line section by means of the medical-device-side connector and can conduct liquid, which the second line section can transfer out of the second line section into the first line section and further into the discharge line in a flushing step of the priming process. For the purposes of the treatment, the second line section can be detached from the connector or the first line section and connected to the patient.

The pump or means for generating the reduced pressure may be one or more pumps from the group including a peristaltic pump, a membrane pump, a centrifugal pump, an impeller pump and a gear pump.

The pump or means for generating the reduced pressure may be one or more pumps from the group including an ultrafiltration pump, a blood pump and a substituate pump.

The pump may be a peristaltic pump and at least one actuator of the peristaltic pump may be part of the first or second shut-off element.

The shut-off element(s) and the enclosing means may each comprise one or more pumps, valves, non-return valves or clamps, or a combination thereof.

The shut-off elements may be manually operated components or may be actuated by the controller. It is also possible for a first shut-off element to be actuated manually and a second shut-off element to be actuated by the controller. A plurality of shut-off elements may also be provided.

The first and/or second line section may be branched. In each case one shut-off element may be provided at each end of the first and/or second line section, except at detachable connection ends of the first and second line section. can be branched.

In the embodiments comprising actuatable shut-off elements, the controller may be programmed to actuate the actuatable shut-off elements in order to enclose the fluid volume. For example, the controller may be programmed to operate the pump in one direction. The controller may also be programmed to close all the shut-off elements arranged upstream in a first step, to operate the pump in a subsequent step, and to close all the shut-off elements arranged downstream in a subsequent step. Alternatively, in the first step, one or more or all the actuatable shut-off elements arranged downstream can also be closed as long as there is an open connection downstream thereof for discharging fluid. This may be a non-return valve or a clamp that is closed manually, for example.

The medical device may comprise a user interface for a user to input an instruction and the controller may be programmed to activate the disconnection mode in response to the instruction being input on the user interface.

When the disconnection mode is activated, a special mode may be activated in the program code of the controller. When the disconnection mode is activated, a special sequence of a program code may be executed, by means of which the medical device carries out the disconnection method. The disconnection mode may also be integrated in another mode. For example, a priming mode may be stored in the program code and the disconnection mode may constitute a step, for example the last step of the priming mode.

The user interface may be a display, a screen, a touchscreen, a keypad, a control knob, a microphone for recording a voice signal or a camera for detecting a user gesture.

The controller may be programmed to activate a plurality of modes and to automatically switch from one of the modes into the disconnection mode.

For example, in a reinfusion mode, the controller may be connected to a sensor of the medical device, for example an optical sensor, which detects that there is no more blood in the tube set. The controller may process this signal in its program code such that another mode can be started. This mode may be a disconnection mode. Alternatively or additionally, an additional mode may be provided in the program code of the controller which, after the reinfusion mode is completed, empties the tube set and/or a dialyzer and/or a machine-side fluidic system, and the controller may be programmed to switch into the disconnection mode after a predetermined time period or after a predetermined fluid volume has been transported or after air or an interface between the blood and a reinfusion liquid having optical properties that are different from blood has been detected by means of a sensor in the region to be emptied or after a predetermined pressure is detected.

Alternatively or additionally, a mode ("priming mode") may be provided in the program code of the controller which, before the treatment starts, fills the tube set or cassette with priming liquid and/or flushes the tube set or cassette with liquid, and the controller may be programmed to switch into the disconnection mode after the priming mode is completed. The controller may be programmed to operate a pump during the priming mode and to thus move liquid from a liquid source towards the tube set or cassette. The controller may be programmed to determine the end of the priming for example by a predetermined time having elapsed, a predetermined liquid volume having been moved into the tube set or cassette, or an air detector or liquid sensor displaying that there is no more air or there is predominantly only liquid.

The controller may also be programmed such that the switch to the disconnection mode is first made automatically, but the pump is only started following an input via the user interface.

The controller may also be programmed to, in particular, only allow an input via the user interface to start the pump if the disconnection mode is activated. In other words, the program code of the controller can provide that there are modes or phases which are not the disconnection mode in which the pump is not started despite a corresponding input via the user interface.

By restricting allowing the disconnection method to start in this way, it may be possible to prevent a disconnection method of this kind from being able to start during the treatment, for example.

As disclosed above, the medical device may comprise neither the first nor the second line section, but instead may solely be connected thereto for the purposes of treatment.

As disclosed above, the medical device may comprise one of the two line sections, and may solely be connected to the second of the two line sections for the purposes of treatment.

In another embodiment, the medical device comprises both the first and the second line section. The first line section may have at least partially an elastic property, wherein the first line section can be deformed from a starting position into a tensioned position by the elastic property, wherein a fluid volume contained in the first line section is lower in the tensioned position than a fluid volume contained in the starting position.

Optionally, one of the two line sections may be part of a disposable item, in particular a tube set or cassette system used as part of blood treatment.

Optionally, both line sections may be part of one or more disposable items, in particular a tube set or cassette system used as part of blood treatment or hydraulics (a machine-side fluidic system through which blood does not flow during the treatment) designed as a disposable item for supplying a dialyzer with dialysate.

The first line section may comprise at least one region which is more elastic than the second line section.

According to an embodiment, the first line section and the second line section may comprise at least one region which is made of a more elastic material than the remainder of the first line section and the second line section, wherein the region of the first line section is made of a more elastic material than the region of the second line section, such that, when the connection between the line sections is detached, fluid is drawn from a connection region of the line sections into the first line section to a greater extent than into the second line section, or vice versa.

The controller may comprise a computer system, for example, and may be implemented in the form of digital circuits, computer hardware, firmware, software or in any combination thereof. The invention may also be implemented in the form of a computer-program product, e.g. a computer program on a physical information carrier (e.g. machine-readable storage medium). The controller may comprise a general processor, a digital signal processor (DSP) for continuously processing digital signals, a microprocessor, an application-specific integrated circuit (ASIC), an integrated circuit consisting of logic elements (FPGA) or other integrated circuits (IC) or hardware components in order to perform the individual method steps. A data-processing program (software) can run on the hardware components to carry out the method steps. A plurality of or a combination of the various components are also possible for controlling the operation thereof.

The controller may further comprise a memory in which the program code is stored, for example a read-only memory (ROM) or random access memory (RAM), or both, magnetic, magneto-optical, optical or solid-state (SSD) storage media, non-volatile storage elements such as semiconductor storage elements (e.g. EPROM, EEPROM), flash-memory devices, magnetic or magneto-optical storage media, CD-ROMs, DVD-ROMs or Blu-ray discs. The memory may also be provided on demand or may be accessible over the Internet (e.g. cloud computing). Suitable data carriers for storing program instructions and data include all types of non-volatile storage elements such as semiconductor storage elements (e.g. EPROM, EEPROM), flash-memory devices, magnetic or magneto-optical storage media, CD-ROMs, DVD-ROMs or Blu-ray discs. The processor and memory elements may be supplemented by special logic modules, or may also be part thereof.

Other features and effects of the present invention become apparent from the following description of selected embodiments of the invention with reference to the appended drawings, in which identical or similar components are denoted by the same reference signs. The features described in the following can be implemented in embodiments that are described above. These embodiments described above are not all set out again in the following. In the drawings:

FIG. 1a shows two line sections, which are used as part of the method for disconnecting two fluid-conducting line sections, and the medical device;

FIG. 1b shows a first line section of the two fluid-conducting line sections in a tensioned position in the example of mechanical deformation;

FIG. 1c shows the first line section from FIG. 1b in a starting position/tensioned position;

FIGS. 8a and 8b show embodiments of the user interface.

Figure 2:
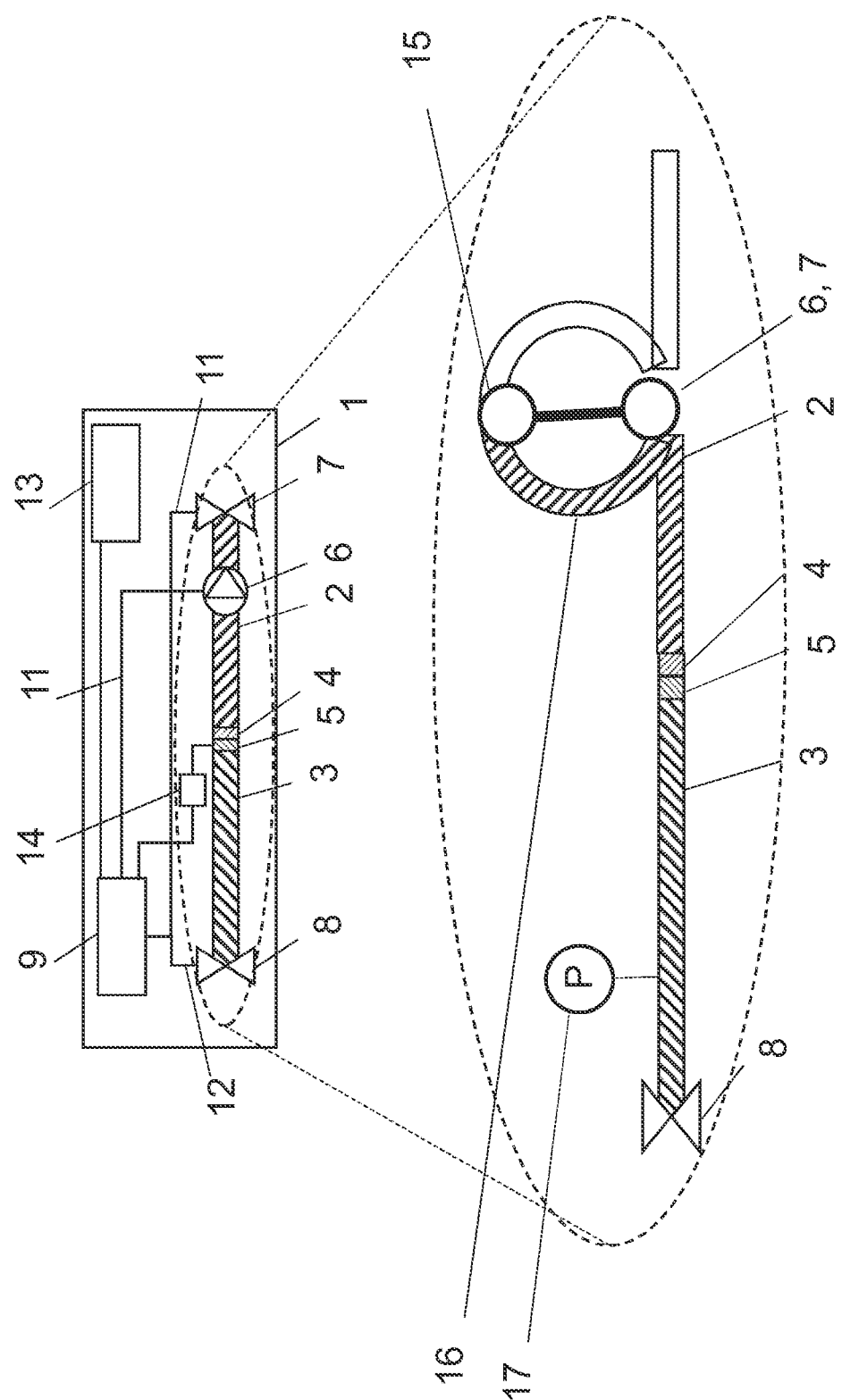
FIG. 2 shows an embodiment comprising a pump as a shut-off element.

When using the method according to the invention, an embodiment of the medical device 1, which is schematically shown in FIG. 1a, comprises two fluidically connected line sections 2, 3 which can be fluidically interconnected via two optional connector elements 4, 5 of the two line sections. The medical device 1 further comprises a pump 6. The first and the second line section each comprise a shut-off element 7, 8 at one end. The line section 2 has at least partially an elastic property, in particular an elastically deformable region. The elastic property or the deformable region may be embodied or arranged between the connection point to the second line section 3 or between the connector element 4 and the shut-off element 7. By means of the pump 6, a reduced pressure can be generated in the first line section 2 or in the first line section 2 and the second line section 3. By means of the reduced pressure, deformation from a starting position into a tensioned position can take place in and/or on the first line section 2, wherein a fluid volume contained in the first line section 2 is lower in the tensioned position than a fluid volume contained in the starting position.

The shut-off elements 7, 8 can be closed and a fluid volume can be enclosed in the two line sections 2, 3 as a result. The shut-off elements 7, 8 can be closed in succession or simultaneously, and in particular a first shut-off element can be closed, then the reduced pressure can be generated, and then the second shut-off element can be closed.

The connection of the line sections 2, 3 can then be detached, wherein the fluid volume contained in the first line section 2 increases compared with the fluid volume in the tensioned position.

The method will be explained on the basis of elastic mechanical deformation with reference to FIGS. 1b and 1c. As described, this is just one of several options for how the elastic property can be implemented.

If the shut-off element 8 is closed at the end of the second line section and the pump 6 pumps fluid or liquid from the first line section 2 towards the second shut-off element 7 (open), reduced pressure is generated at least in a part of the first line section 2. In this process, the volume of the first line section 2 can deform, for example contract inwards (see the arrows in FIG. 1b), such that the volume of the first line section 2 is reduced. If the first and the second line section 2, 3 are enclosed in this state, for example by closing the shut-off element 7 at the end of the first line section 2, the reduced volume of the system remains.

In other words, the walls of the line section 2 thus leave the starting position, which is shown by a schematic dashed line in FIG. 1a, and assume a tensioned position, which is reproduced by a solid line in FIG. 1b.

If the two line sections 2, 3 are detached from one another, the elastically deformable region relaxes owing to the elastic property and the first line section 2 returns towards the starting position from the tensioned position. As shown in FIG. 1c, the walls of the line section 2 thus move further out of the tensioned position (dashed line) towards the starting position or into the starting position (solid line). In this process, fluid can be drawn into the second line section 2 from the connection region or, in other words, from the disconnection region, for example in the region of the connector element 4, to the right in the example shown in FIG. 1a-1c.

Before disconnecting the first line section from the second line section, there may be liquid or a liquid column in the connection region. Without the suction effect due to the relaxation, the liquid column could simply separate and the liquid would flow downwards out of the connection region, at least due to gravity.

In the case described here, when detaching the first line section from the second line section 2, 3, due to the relaxation in the first line section 2, the air can be drawn from the outside inwards in the disconnection region and the fluid column can likewise at least partially follow the suction effect. As a result, more liquid can remain in the first line section 2 overall during the disconnection and a directed flow of the liquid into the first line section 2 can also be achieved.

The risk of contamination of the second line section 2 and/or a leak (escape of liquid to the outside) can thus be reduced.

The medical device 1 may comprise a controller 9. The controller 9 may be programmed to operate the pump to generate the reduced pressure in a disconnection mode. Optionally, the controller 9 may also be programmed to actuate at least one or both shut-off elements 7, 8. For this purpose, the controller can be connected to the respective components to be actuated (pump 6, shut-off elements 7, 8, for example) via signal lines 10, 11, 12 of the medical device 1. The controller 9 may be programmed to start and/or stop the pump 6, for example.

For example, the controller may be programmed to start the pump 6 when the first valve 7 is closed or the valve 8 is closed and to close the other valve 7, 8 such that an enclosed volume is produced in which reduced pressure is applied or the deformable region has deformed.

The medical device 1 may comprise a user interface 13. The user interface 13 may be configured for a user to input an instruction and the controller 9 may be programmed to activate the disconnection mode in response to the instruction being input on the user interface 13.

The line sections 2, 3 are not necessarily both part of the medical device 1, but instead one or both of the line sections 2, 3 can be connected to the pump 6 and the shut-off elements 7, 8 only when the medical device 1 is being used.

The medical device 1 may comprise the first line section 2 and/or the second line section 3. The first line section 2 and/or the second line section 3 may be part of a device-side fluidic system of the medical device 1.

The first line section 2 and/or the second line section 3 may be part of a disposable item.

The pump 6 may be arranged along the first line section 2 and/or the second line section 3 or a point in the fluidic system outside the two line sections 2, 3 which is fluidically connected to the two line sections 2, 3. For example, the pump 6 may be arranged on the side of the shut-off elements 7, 8 arranged on the far side of the connectors 3, 4. The pump 6 only needs to be able to remove liquid from the elastically deformable region.

The medical device 1 may comprise an automatic disconnection device 14. This automatic disconnection device 14 may, for example, comprise a motor which moves the first and/or the second line section 2, 3 and therefore detaches the connection between the first and the second line section 2, 3. The controller 9 may be programmed to actuate the automatic disconnection device 14. This can make it possible for the hygienic disconnection method to be carried out fully automatically, i.e. without human intervention.

FIG. 2 shows an embodiment in which a pump 6 acts as a shut-off element 7 or as means for enclosing a fluid volume. The view in FIG. 2 is not an enlargement, but instead is supposed make it easier to compare the components of the respective embodiments of the medical device 1, as schematically shown in FIG. 1. Some or all of the controller 9, the user interface 13, the signal lines 10, 11, 12 and the automatic disconnection apparatus 14 can be present in this embodiment, and reference is made to the description of FIGS. 1a to 1c in this regard. Configurations of the controller 9, the user interface 13, the signal lines 10, 11, 12 and the automatic disconnection apparatus 14, which are described in the following, can also be present in the medical device 1, if this is technically possible, as described in conjunction with FIG. 1a to 1c. The same applies to FIGS. 3 to 8a.

The pump 6 may be a peristaltic pump and an actuator 15 may be engaged with the first tube section 2 in the region of a line loop 16. As a result, the closed fluid volume can be formed.

In this example, the pump 6 is a roller pump (an embodiment of a peristaltic pump) and the line loop 16 is inserted into the pump 6.

Before disconnecting the line sections 1 and 2, the rollers of the pump 6 are moved into a predetermined disconnection position such that at least part of the line loop 16 is within the second section (between the connection point and the fluidic shut-off point of the pump 6), and remain in this closing configuration during the disconnection. In this example, the pump 6 acts as the shut-off element on the side of the first line section 2. On the device side, the valve 8 acts as the shut-off element. The pump 6 also serves to generate the reduced pressure in the interconnected line sections 1 and 2.

The rollers of the pump 6 perform at least one rotation by a predetermined angle to generate reduced pressure. If the position of the rollers at the start of the process is such that the angle is no longer large enough, two rollers can additionally be rotated by a full revolution or a half revolution. The rotation can also take place until a predetermined reduced pressure is reached.

A pressure sensor 17 may be provided in the medical device 1, which measures the pressure in the enclosed volume and, if necessary, in cooperation with the user interface 13, displays the pressure or displays whether the reduced pressure is sufficient, and/or the controller 9 displays that the pump 6 needs to be rotated further.

The controller may be programmed to actuate the pump accordingly.

When detaching the first line section from the second line section 1, 2, the second line section 2 or the region 16 thereof moves back into the starting position and fluid is drawn into the second line section 2 or the region 16 thereof.

Figure 3:
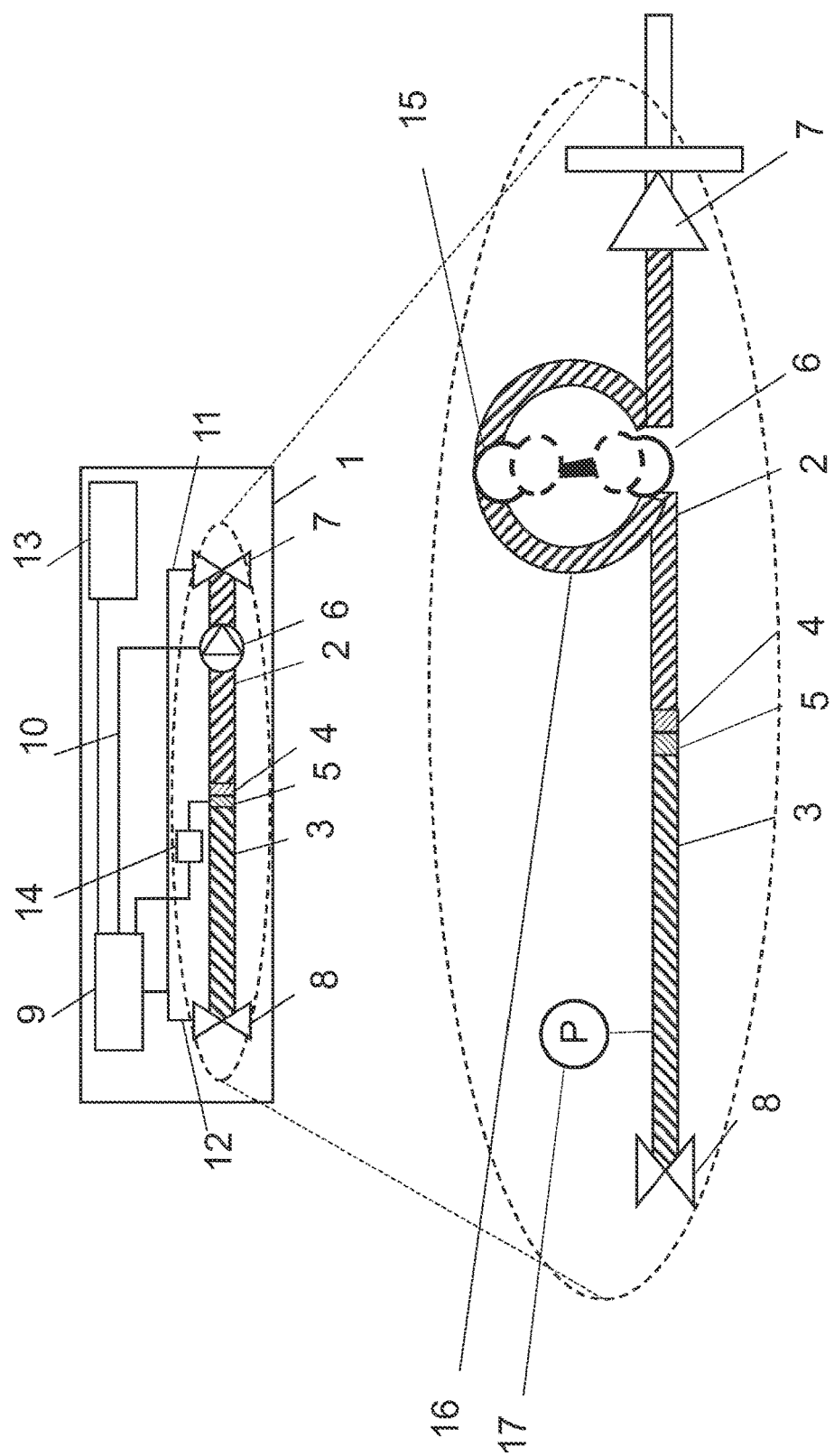
FIG. 3 shows an embodiment comprising a non-return valve as a shut-off element.

As shown in FIG. 3, a pump 6 may be used in combination with a shut-off member 8 in the form a non-return valve. The first line section 2 is thus fluidically closed by the non-return valve, the forward direction of which extends away from the connector or the second line section 3.

By means of the pump 6, fluid, in particular liquid, is conveyed through the non-return valve 8, as a result of which the first line section 2, in particular the region 16 thereof, is brought into a tensioned position. In this embodiment, the enclosed volume can already be present before the pump is started. When the pump is operated, fluid is removed from the region of the first and/or second line section 2, 3.

Various types of pump can be used in this embodiment, for example, since occluding properties are not required for enclosing the fluid volume in this example; e.g. a peristaltic pump 6 comprising retractable actuators, a gear pump, impeller pump, centrifugal pump or membrane pump can be used.

The non-return valve may also be present in the embodiment described in conjunction with FIG. 2, however. As a result, additional protection is provided such that no liquid gets into the region of the connection between the two line sections, since both the blocking effect of the non-return valve and the shut-off effect of the actuator have to be overcome. An additional measure of this kind may be useful in particular in peristaltic pumps, since the design requires the rollers to be regularly spring-mounted and to lift up under excessive force, and therefore they can lose their occluding function.

The level of the generated reduced pressure can be set by a predetermined number of pump revolutions/actuations of the fingers of a finger pump or by means of a predetermined reduced pressure. This control or monitoring can be carried out by the controller 9.

When detaching the first and the second line sections 1 and 2, the second line section 2 or the region 16 thereof moves back into the starting position and fluid is drawn into the second line section 2 or the region 16 thereof.

Figure 4:
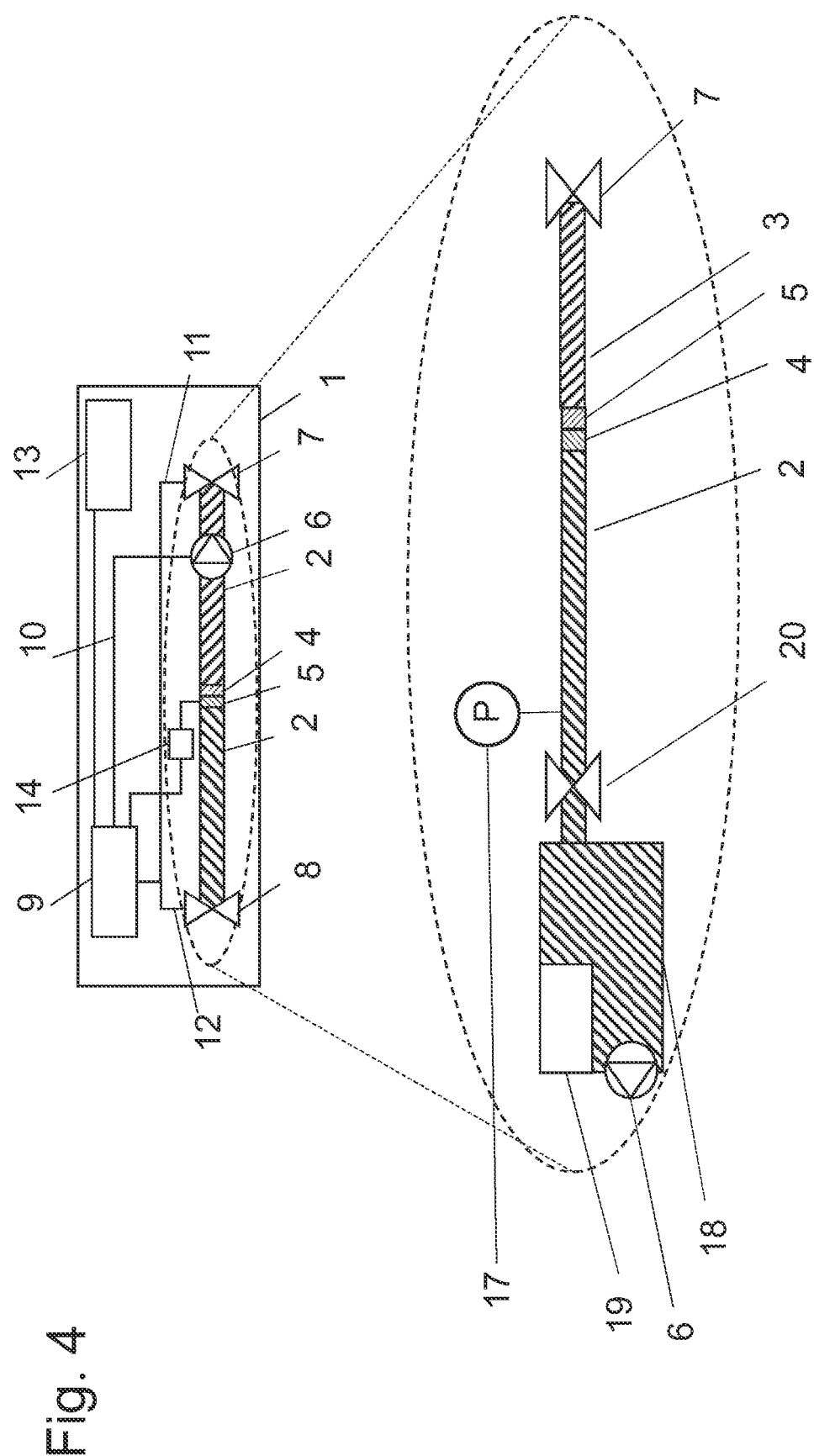
FIG. 4 shows an embodiment comprising hydraulics as part of the first line section.

The medical device 1, as schematically shown in FIG. 4, may comprise device-side hydraulics 18, which may be fluidically connected to the first line section 2 or may form part of the first line section 2. The device-side hydraulics 18 may be fluidically closed by means of one or more shut-off elements. The device-side hydraulics 18 may comprise a gas reservoir 20. When operating the medical device 1, the first and the second line section 2, 3 and the hydraulics 18 can be filled with liquid, with the exception of the gas reservoir 19. A pump 6 may be provided in order to generate the reduced pressure. The pump 6 may be a pump which pumps a liquid during blood treatment, for example which pumps dialysate during dialysis treatment. The pump 6 may be an ultrafiltration pump or a balancing pump.

In an arrangement of this kind, fluid can be drawn towards the first line section 2 as part of one of the device-side hydraulics 18. This arrangement may be used if a liquid-filled tube set, for example after priming, which is at least partially formed by the second line section 3 is intended to be removed from the first line section 1 and is then intended to be connected to a patient. As a result, the second line section 3 may potentially be kept in a more hygienic state.

The medical device 1 may comprise a shut-off means 20. The shut-off means 20 can be opened or the controller 9 can be programmed to open said means before the reduced pressure is generated. As a result, the volume in which the reduced pressure acts can be increased (by the additional volume of the hydraulics 18), or the fluid volume of the first line section 2 can be increased and/or the gas reservoir can be part of the first line section 2. This may give the first line section 2 a more elastic property than if the shut-off element 20 were closed. Therefore, it is possible to enhance the effect of the relaxation out of the tensioned position.

The device-side hydraulics 18 may comprise a region made of an elastic material. The region can be moved into a tensioned position by the generated reduced pressure.

Figure 5A:
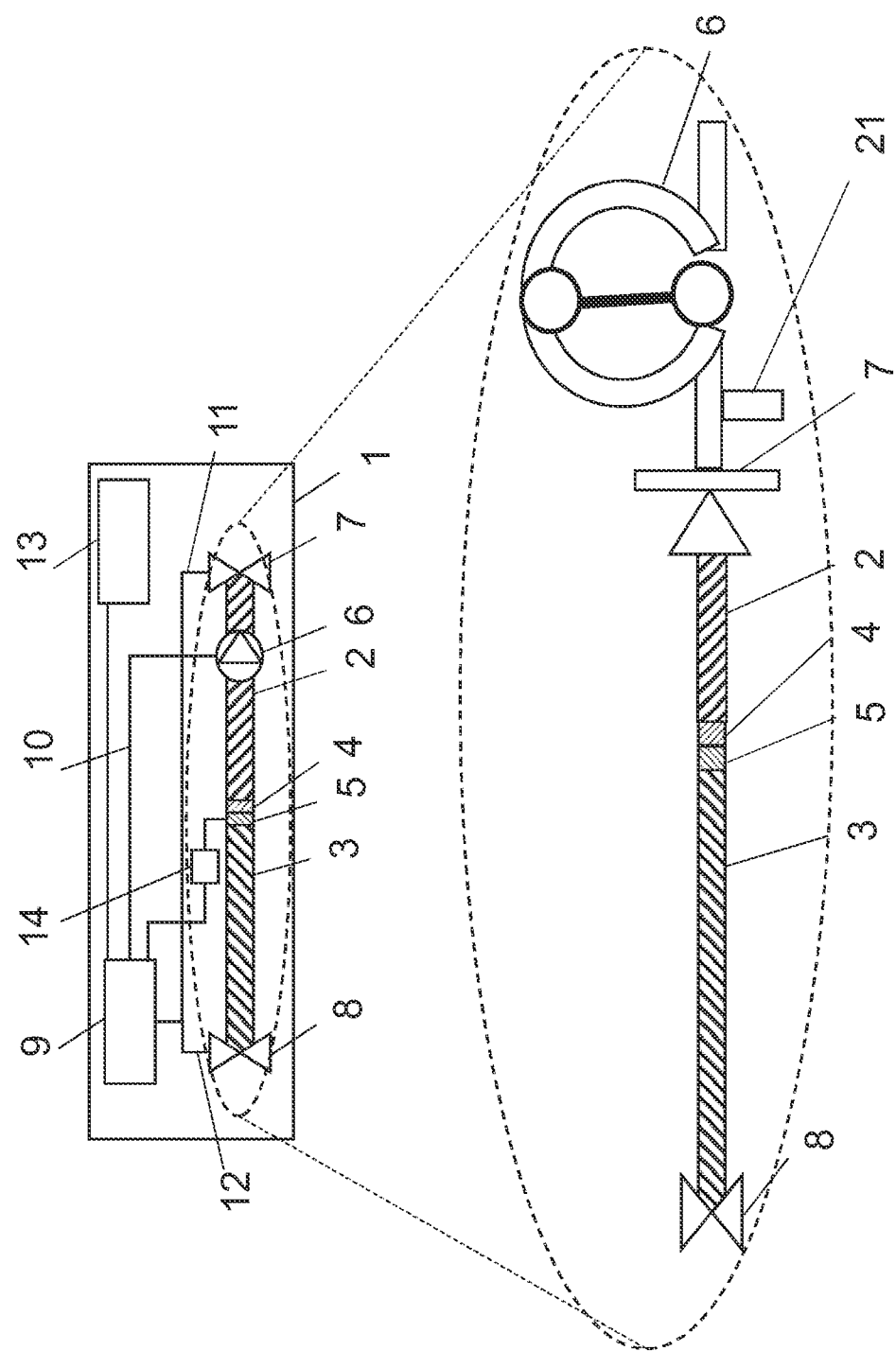
FIG. 5a shows an embodiment comprising a pump arranged on the outside.
Figure 5B:
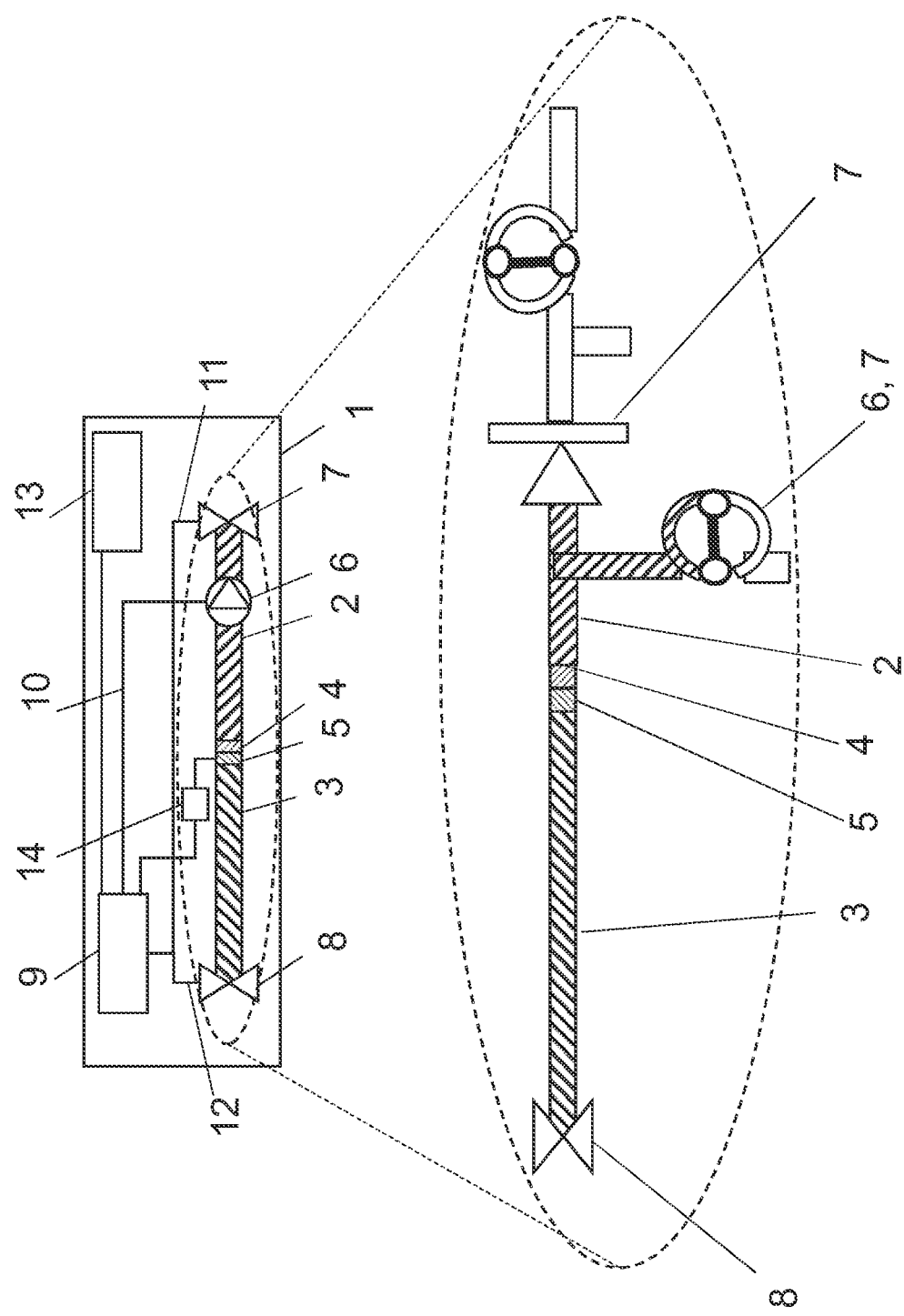
FIG. 5b shows an embodiment comprising a branched line section.

FIGS. 5*a* and 5*b* show further embodiments of the medical device 1. This embodiment differs from the embodiments as described in FIGS. 2 and 3 in that the pump 6 is arranged outside the first line section 2. The shut-off element 8 may be a non-return valve, but it may also be another shut-off element described in this description.

The pump 6 may be a blood pump of a blood-treatment machine. The blood pump may be configured to pump blood in a blood line 21 during blood treatment. The first line section 2 may be a liquid-supply line. During treatment, liquid can be transferred into the blood line 21 from the first line section 2.

The line section 2 or at least a region thereof can be brought into a tensioned position by the reduced pressure generated by means of the pump 6 arranged outside, such that fluid is drawn into the second line section 2 when the line sections 2 and 3 are detached.

FIG. 5*b* shows a variant of the embodiment from FIG. 5*a*, in which a branch to the pump 6, for example a substitute pump for hemodiafiltration treatment, is additionally provided in the first line section 2. In this embodiment, the pump 6 also assumes the function of the shut-off element 7 for this branch of the first line section 2. Here, the reduced pressure can be generated in the first line section 2 by the pump 6.

Figure 6A:
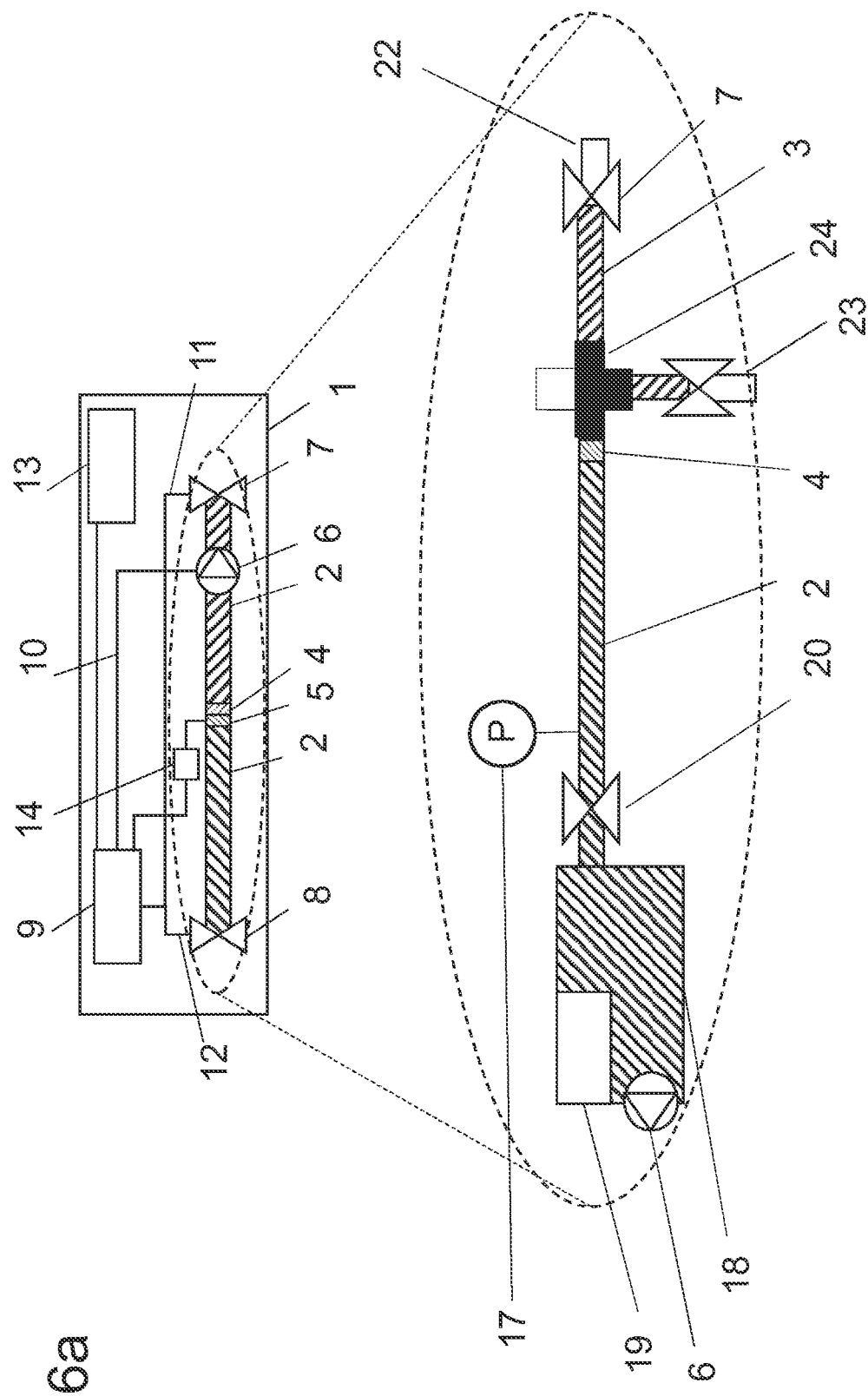
FIG. 6a shows an embodiment comprising a T-piece or Y-piece for connecting two lines.
Figure 6B:
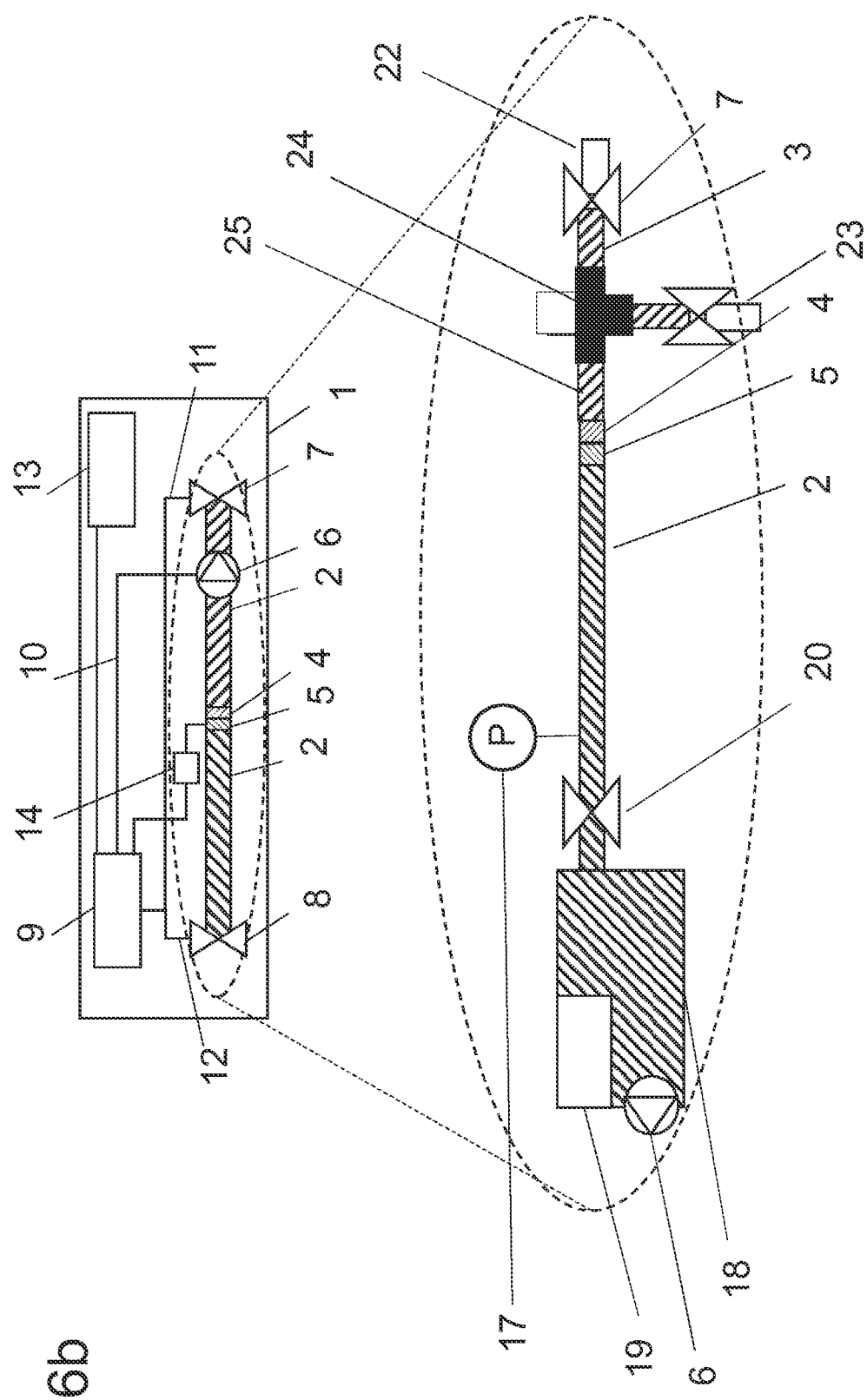
FIG. 6b shows an embodiment in which the T-piece or Y-piece is arranged at one end of a line section.

FIGS. 6*a* and 6*b* show embodiments of the medical device 1 as described in conjunction with FIG. 4. In this embodiment, the second line section 3 comprises, as disposable items, at least parts of an arterial line 22 and a venous line 23, which are interconnected by a T-piece 24. As shown in FIG. 6*a*, the T-piece 24 may be directly connected to the first line section 2, for example via a discharge port of a blood-treatment machine. In the embodiment shown in FIG. 6*b*, the T-piece 24 is not directly connected to the first line section 2, for example a discharge port of a blood-treatment machine, but instead via another line section 25. The T-piece 24 may also be in the shape of a Y-piece. The discharge port may also be what is known as a flushing port, by means of which flushing liquid can be transferred out of the second line section 3 into the first line section 2 when flushing the arterial line 22 and/or venous line 23.

The configuration as described in conjunction with FIGS. 6*a* and 6*b* may in particular be used when priming/filling the tube set/disposable item before the start of treatment. When disconnecting the first and second line sections 2, 3, fluid is preferably intended to be drawn towards the first line section (to the device-side hydraulics 18).

Figure 7A:
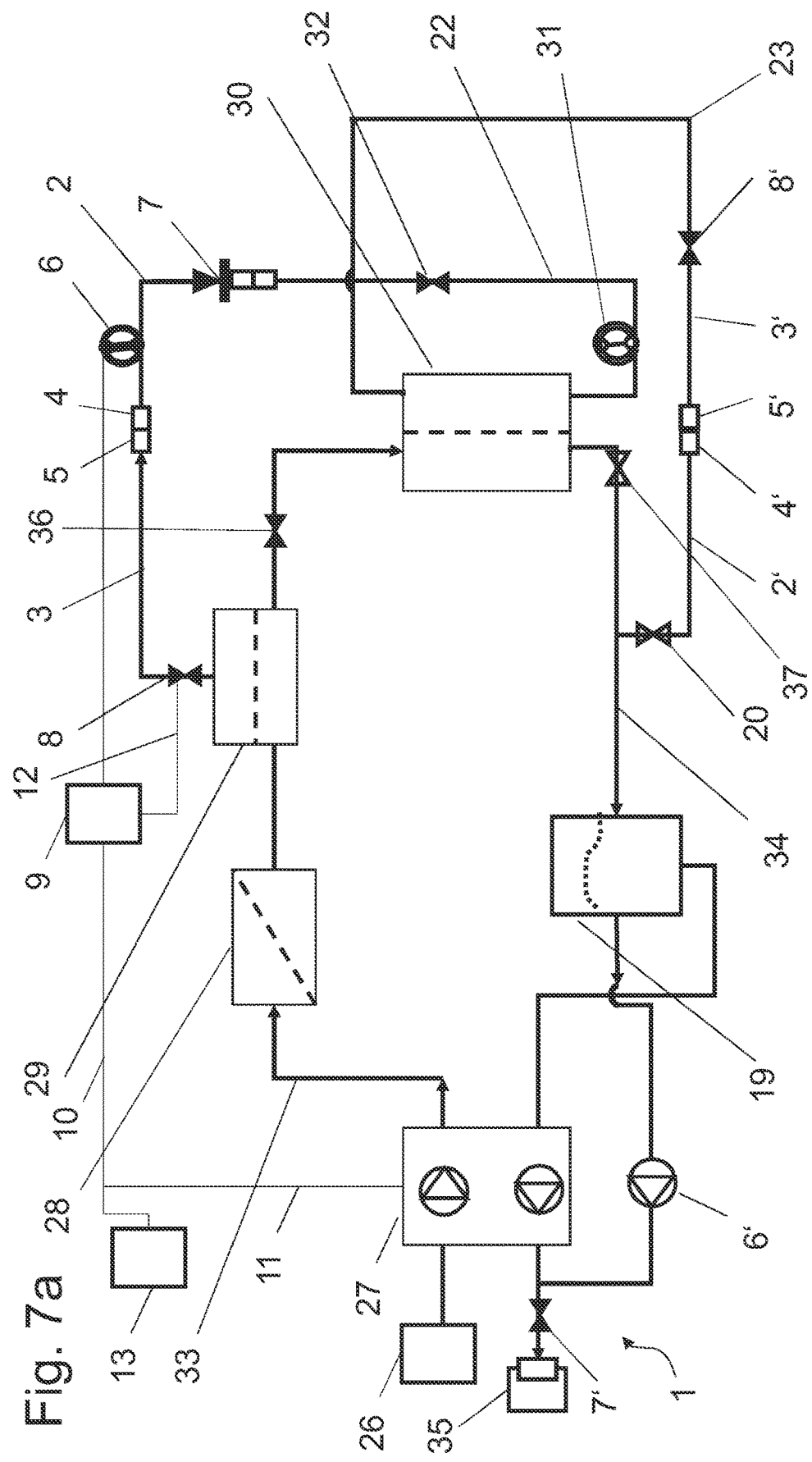
FIG. 7a shows an embodiment of a medical device.
Figure 7B:
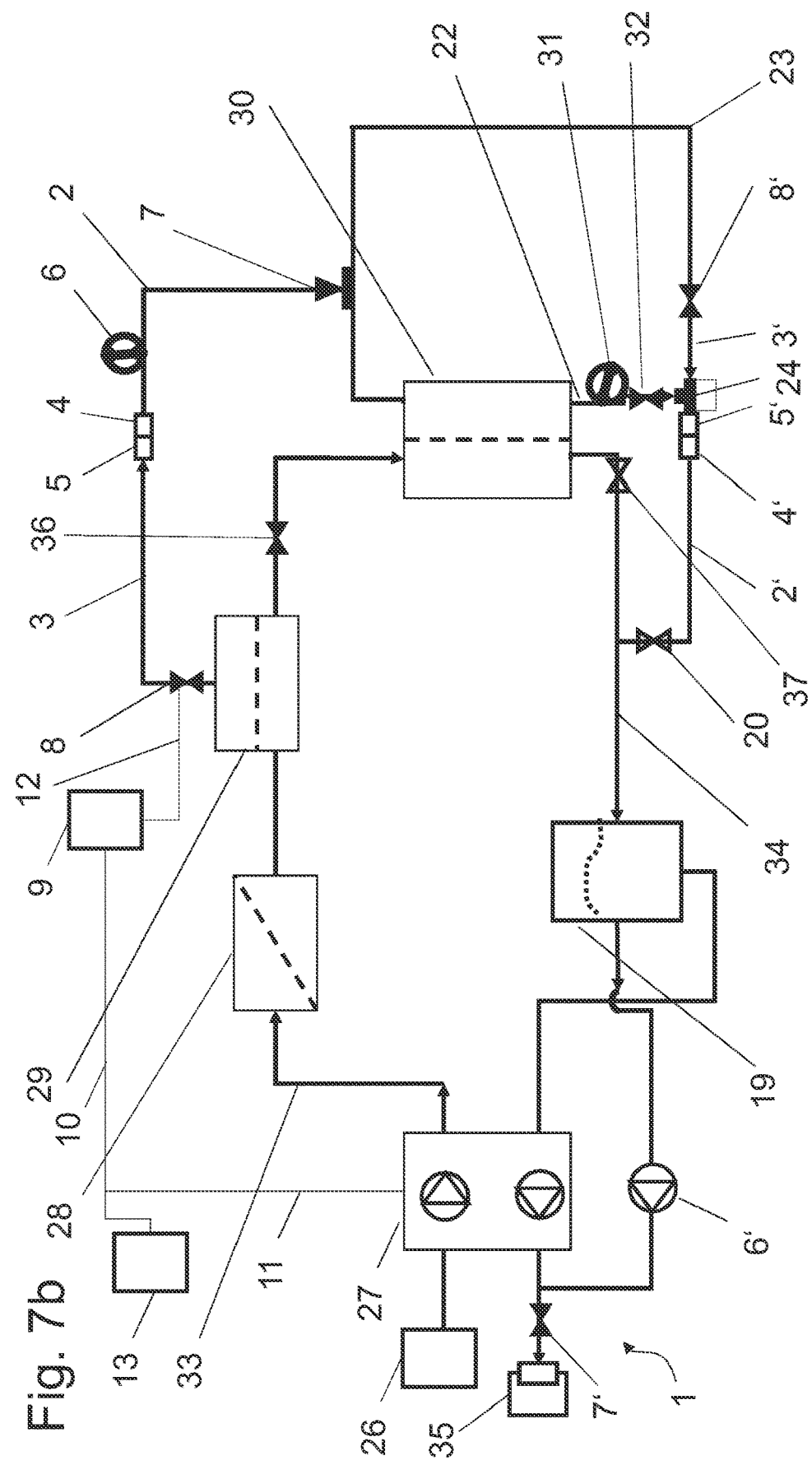
FIG. 7b shows an embodiment of the medical device in another configuration.

FIGS. 7*a* and 7*b* schematically show embodiments of the medical device 1 in the form of a dialysis machine. In the drawings, some components are optional; in particular, some components can be designed as disposable items and do not have to be fixed components of the medical device 1. The dialysis machines differ merely in respect of their disposable items and/or the configuration of the guidance of the lines. There may be two disconnection points (reference signs 2, 3, 4, 5 on one hand and reference signs 2', 3', 4', 5' on the other) or only one of the two disconnection points in the medical device 1. The two embodiments are provided by way of example. The disconnection point may be a connection point at the inflow of liquid into the extracorporeal blood-line system, for example the connection point of the first line section 2 to the second line section 3, or connectors 4, 5 arranged at the respective ends thereof. The disconnection point may be a connection point at the discharge from the extracorporeal blood-line system, for example the connection point of the first line section 2' to the second line section 3', or connectors 4', 5' arranged at the respective ends thereof. The embodiments or configurations in this description may also be provided instead of the components and configurations that are explicitly described here.

The dialysis machine in the form of the medical device 1 comprises or may comprise the following components:

A liquid source 26, a balancing system comprising a pump 27, a first sterile filter 28 (optional), a second sterile filter 29 (optional), a dialyzer 30 (optional), a ventilation chamber 19 (optional), an ultrafiltration pump 6' (optional), a priming or substitute port 5, a priming or substitute pump 6 (optional), a discharge port 4', a blood pump 31, a controller 9, a user interface 13, signal lines 10, 11, 12 (only a selection shown), a venous clamp 8', an arterial clamp 32 (optional), a pre-dialyzer shut-off element 36 (optional), a post-dialyzer shut-off element 37 (optional), a first discharge-line shut-off element 7' (optional), a first priming-line shut-off element 8, a second priming-line shut-off element 7, a discharge shut-off element 20 (optional), and a T-piece or Y-piece 24 (optional).

The components may be connected to liquid-conducting lines as follows: The liquid, generally a physiological liquid or dialysate, is pumped from the liquid source 26 into a dialysate line 33 through the balancing system 27, optionally through the first sterile filter 28, to the dialyzer 30, and is then discarded from the dialyzer 30 in a discharge line 34, optionally through a ventilation chamber 19, again through the balancing system 27 into a discharge 35 (not part of the medical device 1). The dialysate line 33 may comprise a branch line, in the form of a second line section 3, for example optionally via a second sterile filter 29, which can be guided via a priming or substitute port 5 to a priming or substitute line, in the form of a second line section 2. This priming or substitute line 2 may be connected to an arterial blood line 22 or a venous blood line 23. Liquid, e.g. blood during the treatment or priming or flushing liquid in the priming phase, can be pumped by means of a blood pump 31 in the blood line(s) 22, 23. The balancing system ensures that only a predetermined quantity of liquid is removed from the patient. Various balancing systems are known, for example the quantity of liquid that is pumped to the patient and the quantity that is pumped away from the patient can be determined by flow measurement and the delta, as prescribed, can be set such that a desired ultrafiltration rate, in other words a net balance rate, is implemented. Another balancing system is shown in FIGS. 7*a* and 7*b*. In these figures, the same volume is pumped to the patient as is pumped away from the patient by means of a volumetric balancing system 26, for example. An ultrafiltration pump 6' connected in parallel therewith additionally pumps liquid away from the patient and thus produces the net balance or ultrafiltration rate.

In addition, the medical device 1 may also comprise a series of shut-off elements. For example, the device 1 may comprise a venous shut-off element 8' (venous clamp), an arterial shut-off element 32 (arterial clamp), a pre-dialyzer shut-off element 36, a post-dialyzer shut-off element 37, a first discharge-line shut-off element 7' and a first and second priming-line shut-off element 7, 8.

The difference between the embodiments shown in FIGS. 7a and 7b consists in that, in the embodiment shown in FIG. 7a, the priming or substitute line 2 is connected to one end of the arterial blood line 22 (normally the end connected to the patient during treatment) and only the venous blood line 23 is connected to the end (normally the patient-side end) comprising the discharge port 4'. In the embodiment shown in FIG. 7b, the priming or substitute line 2 is connected to a port arranged along the venous blood line 23 and in addition, the end of the arterial blood line 22, which is normally on the patient side, is connected to the drain or rinse port 4'. In another embodiment, the priming or substitute line is connected to a port arranged along the arterial blood line.

The following components or lines may in particular be designed as disposable items: the dialyzer 30, the arterial blood line 22, the venous blood line 23, or the priming or substitute line 2. These lines can together form a tube set or cassette system. A cassette system means that at least two of these lines are detachably interconnected and/or the lines are at least partially formed by flexible tubes, and otherwise by dimensionally stable channels.

The medical device 1 may for example be configured to fill the tube set or cassette system with physiological liquid before the treatment. For this purpose, the controller 9 may for example be programmed to transfer liquid from the liquid source 26 into the tube set or cassette system via the priming or substitute port 4 by means of the pumps of the balancing system 27, for example in a filling mode, which can also be called a priming mode. In another method step, for example a flushing mode, the tube set or cassette system can be flushed after filling, wherein liquid is flushed through the tube set or cassette system and is flushed through the discharge port 4' into the discharge line 34. For the treatment, the venous line 23 must be connected to the patient. For this purpose, for example in the embodiment in FIG. 7a, the end of the venous line that is connected to the discharge port 4' by the optional transition piece 5' is detached from the discharge port 4'. Before this detaching takes place, however, which can be carried out manually or automatically, the controller 9 causes at least a first line section 2', which is connected to the discharge port 4', and a part of the venous line as the second line section 3' to be closed at least on the side of the venous line 23. The controller may actuate the ultrafiltration pump 6', for example, and may pump liquid away by means of said pump such that reduced pressure is generated. Owing to the elastic property of the first line section 2', at least part of the first line section 2' deforms into a tensioned position. The first line section 2' may also be more elastic than the second line section 3'. The controller can then actuate at least one shut-off element 7', and optionally a plurality of shut-off elements, in order to keep the system in this tensioned position. When subsequently detaching the second line section 3' from the drain or rinse port 4', which is optionally carried out manually or automatically, the first line section 2' can relax.

It should be noted at this point that the medical devices 1 as described in conjunction with FIGS. 7a and 7b may also comprise one or more of the following components having the functions as described in the description: a gas reservoir 19, a valve 20 for increasing the elastic property of the first line section 2', or a pressure sensor (not shown).

The medical device 1 may also be configured for a disconnection step after the treatment. For this purpose, the controller 9 can close the shut-off element 8 and operate the pump 6. The pump 6 may be a peristaltic pump in the form of a substitute pump. Alternatively, the blood pump 31 can also be used to generate reduced pressure in the line section 2 or to pump liquid out of said line section. The shut-off element 7 may be a non-return valve and may also be part of a transition piece or part of the arterial tube 22, and therefore it is not necessary to actively close this shut-off element.

In other configurations of the shut-off element 7, the controller may be programmed to close the shut-off element 7 after operation of the pump 6. Owing to the elastic property of the first line section 2, at least part of the first line section 2 deforms into a tensioned position. The first line section 2 may also be more elastic than the second line section 3. When subsequently detaching the second line section 3 from the priming or substitute port 5, which is optionally carried out manually or automatically, the first line section 2 can relax.

FIGS. 8a and 8b schematically show the user interface 13. The user interface 13 may comprise a screen 38 and at least one button 39. The screen 38 may be a touchscreen and the button 39 may be designed as a soft key, i.e. a button to be pressed on the touchscreen, as shown in FIG. 7a. The button 39 may also be designed as a hard key, i.e. a button provided separately from the screen, as shown in FIG. 7b. The controller 9 may be configured to transmit instructions to the user interface 13 via a data line or to receive such instructions therefrom. For example, the user interface 1 may be programmed to cause the controller to switch into the disconnection mode or to start the disconnection mode once the button 39 is pressed. The controller 9 may be programmed to perform a method sequence and to send a message 40, for example for display on the user interface 13 when one or more or all of the following situations have occurred or the controller arrives at this point when executing a program: the program sequence allows activation of the disconnection mode, the disconnection mode can be started, the connection can be detached once the method steps to be performed by the machine have been completed, a disinfection process must be carried out, for example because the controller has detected that a treatment is supposed to be prepared or carried out or a sensor, for example a pin which displays the presence of a disposable item, displays to the controller that a disposable item has been removed from the machine without the method steps to be performed by the machine having been completed.

Where reference is made to an embodiment here, this should be understood to be a purely exemplary embodiment according to the invention.

Embodiments according to the invention may have one or more of the above-mentioned features in any combination, provided that the specific embodiment does not appear to be technically impossible to a person skilled in the art.

The invention claimed is:

1. Medical device, configured to receive at least two fluid-conducting line sections that can be detached from one another, wherein a first line section of the two fluid-conducting line sections has at least partially an elastic property, comprising
   at least a first and a second shut-off element for enclosing a fluid volume in the two line sections,
   a pump for generating a reduced pressure in the two line sections, as a result of which elastic deformation from a starting position into a tensioned position takes place in and/or on the first line section, a controller for actuating the pump, wherein the controller is programmed to operate the pump to generate the reduced pressure in a disconnection mode, wherein the controller is programmed to close one of the shut-off elements before generating the reduced pressure, to close the fluid volume on one side and/or to close one of the shut-off elements for enclosing the fluid volume after generating the reduced pressure.

2. Medical device according to claim 1, comprising the first or the second line section, wherein this line section is part of a device-side fluidic system of the medical device.

3. Medical device according to claim 2, comprising a fluid source for a physiological liquid, fluidically connected to the second line section, optionally, a sterile filter fluidically arranged between and connected to the fluid source and the second line section, and optionally a medical-device-side connector on one end of the second line section for connection to one end of the first line section.

4. Medical device according to claim 2, comprising discharge line, wherein the first line section is fluidically connected to the discharge line or is part thereof, a medical-device-side connector on one end of the first line section for connection to one end of the second line section.

5. Medical device according to claim 1, wherein the pump is a peristaltic pump and at least one actuator of the peristaltic pump is part of the first or second shut-off element or is the first or second shut-off element.

6. Medical device according to claim 1, wherein the pump is an ultrafiltration pump and/or a blood pump and/or a substituate pump of an extracorporeal blood-treatment machine or a dialysis machine.

7. Medical device according to claim 1, comprising a user interface for a user to input an instruction, wherein the controller is programmed to activate the disconnection mode or to start the pump in response to the instruction being input on the user interface, and/or wherein the controller is programmed to activate a plurality of modes and to automatically switch from one of the modes into the disconnection mode.

8. Medical devices according to claim 2, comprising the other line section of the two line sections, wherein the first line section has at least partially an elastic property, wherein a fluid volume contained in the first line section is lower in the tensioned position than a fluid volume contained in the starting position, and wherein, optionally, the other line section of the two line sections is part of a disposable item that is a tube set or cassette system used as part of blood treatment, or, optionally, both line sections are part of one or more disposable items that is a tube set or cassette system used as part of blood treatment.

9. Medical devices according to claim 8, wherein the first line section comprises at least one region which is more elastic than the second line section.

10. Medical devices according to claim 8 wherein the first line section and the second line section comprise at least one region which is more elastic than the remainder of the first line section and the second line section.

11. Method for disconnecting two fluid-conducting line sections of a medical device according to claim 1, which are detachably interconnected, comprising the steps of:

enclosing fluid volume in the two line sections, generating the reduced pressure in the two line sections, as a result of which elastic deformation from the starting position into the tensioned position takes place in and/or on the first line section, wherein a fluid volume contained in the first line section is lower in the tensioned position than a fluid volume contained in the starting position, and detaching the connection of the line sections, wherein the fluid volume contained in the first line section in the tensioned position increases.

12. Method according to claim 11, wherein the first line section comprises at least one region which is more elastic than the second line section.

13. Method according to claim 11, wherein the first line section and the second line section comprise at least one region which is more elastic than the remainder of the first line section and the second line section.

14. Method according to 11, wherein the elastic property is provided by an elastic material and/or a geometry having elastic restoring force and/or an enclosed gas.

15. Method according to claim 11, wherein the first line section is part of a device-side fluidic system of the medical device, and the second line section is part of a disposable item, or the second line section is part of a device-side fluidic system of the medical device, and the first line section is part of a disposable item.

16. Method according to claim 11, wherein there is substantially only a physiological fluid and no blood in the first and the second line section.

* * * * *